(12) United States Patent
Mohamed et al.

(10) Patent No.: US 8,808,760 B2
(45) Date of Patent: Aug. 19, 2014

(54) EXTRACT FROM PALM LEAVES AND A METHOD FOR PRODUCING THE SAME

(75) Inventors: Suhaila Mohamed, Selangor (MY); Juliana Jafri, Selangor (MY); Noordin Mohamed Mustapha, Selangor (MY); Intan Natasya Ahmad, Selangor (MY); Mursyida Abdul Razak, Selangor (MY)

(73) Assignee: Universiti Putra Malaysia, Selangor (MY)

( * ) Notice: Subject to any disclaimer, the term of this patent is extended or adjusted under 35 U.S.C. 154(b) by 670 days.

(21) Appl. No.: 12/668,311

(22) PCT Filed: Jul. 9, 2008

(86) PCT No.: PCT/MY2008/000065
§ 371 (c)(1),
(2), (4) Date: Aug. 23, 2010

(87) PCT Pub. No.: WO2009/008697
PCT Pub. Date: Jan. 15, 2009

(65) Prior Publication Data
US 2011/0003019 A1    Jan. 6, 2011

(30) Foreign Application Priority Data
Jul. 11, 2007  (MY) .............................. PI20071111

(51) Int. Cl.
*A61K 36/889* (2006.01)
*A23L 1/30* (2006.01)

(52) U.S. Cl.
CPC .......... *A61K 36/889* (2013.01); *A23V 2002/00* (2013.01); *A23L 1/3002* (2013.01)
USPC ........................................ 424/727; 424/774

(58) Field of Classification Search
CPC .................................................... A61K 36/889
USPC ................................................ 424/727, 774
See application file for complete search history.

(56) References Cited

U.S. PATENT DOCUMENTS

| 4,428,969 | A  | * | 1/1984 | Muller et al. ................... 426/53 |
| 2007/0036821 | A1 |  | 2/2007 | Daniels |

FOREIGN PATENT DOCUMENTS

| BG | 62593 B1 | 3/2000 |
| JP | 09206043 A | 8/1997 |
| WO | 2006090198 A3 | 4/2009 |

OTHER PUBLICATIONS http://www.botany.hawaii.edu/faculty/carr/arec.htm—accessed Jan. 2013.*
Salleh (Journal of Agricultural and Food Chemistry (2002), vol. 50, pp. 3693-3697).*
Anderson (Canadian Journal of Cardiology (2013), vol. 29, pp. 151-167).*
Trine et al. (Asean Food Journal (2003), vol. 12, No. 3, pp. 137-147).*
Ngando Ebongue, G.F., R. Dhouib, F. Carriere, P.-H. Amvam Zollo, and V. Arondel. "Assaying Lipase Activity from Oil Palm Fruit (*Elaeis guineensis* Jacq.) Mesocarp." Plant Physiology and Biochemistry 44 (2006): 611-17.
Sambanthamurthi, R., N. Rajanaidu, and S. Hasnah Parman. "Screening for Lipase Activity in the Oil Palm." Biochemical Society 26.6 (2000): 769-70.
Edem, D.O. "Palm Oil: Biochemical, Physiological, Nutritional, Hemotalogical, and Toxicological Sspects; A Review." Plant Foods for Human Nutrition 57 (2002): 319-41.
Ebong, P.E., D.U. Owu, and E.U. Isong. "Influence of Palm Oil (*Elaesis guineensis*) on Health." Plant Foods for Human Nutrition 53 (1999): 209-22.
Chong, Yh, and Tk Ng. "Effects of Palm Oil on Cardiovascualr Risk" [Abstract] Med J Malaysia 46.1 (1991): 41-50. Unbound Medline. Web. Jun. 23, 2010. <http://www.unboundmedicine.com/medline/ebm/record/1836037/abstract/Effects_of_palm_oil_on_cardio-vascular_risk_>.

* cited by examiner

*Primary Examiner* — Susan Hoffman
(74) *Attorney, Agent, or Firm* — Preston Smirman; Smirman IP Law, PLLC

(57) ABSTRACT

A method for preparing an herbal extract comprises the steps of pre-treating foliages derive from a plant of Arecaceae family; extracting the pre-treated foliages by using a polar solvent; removing the pre-treated foliages from the used polar solvent; and concentrating the used polar solvent to acquire the herbal extract.

7 Claims, 3 Drawing Sheets

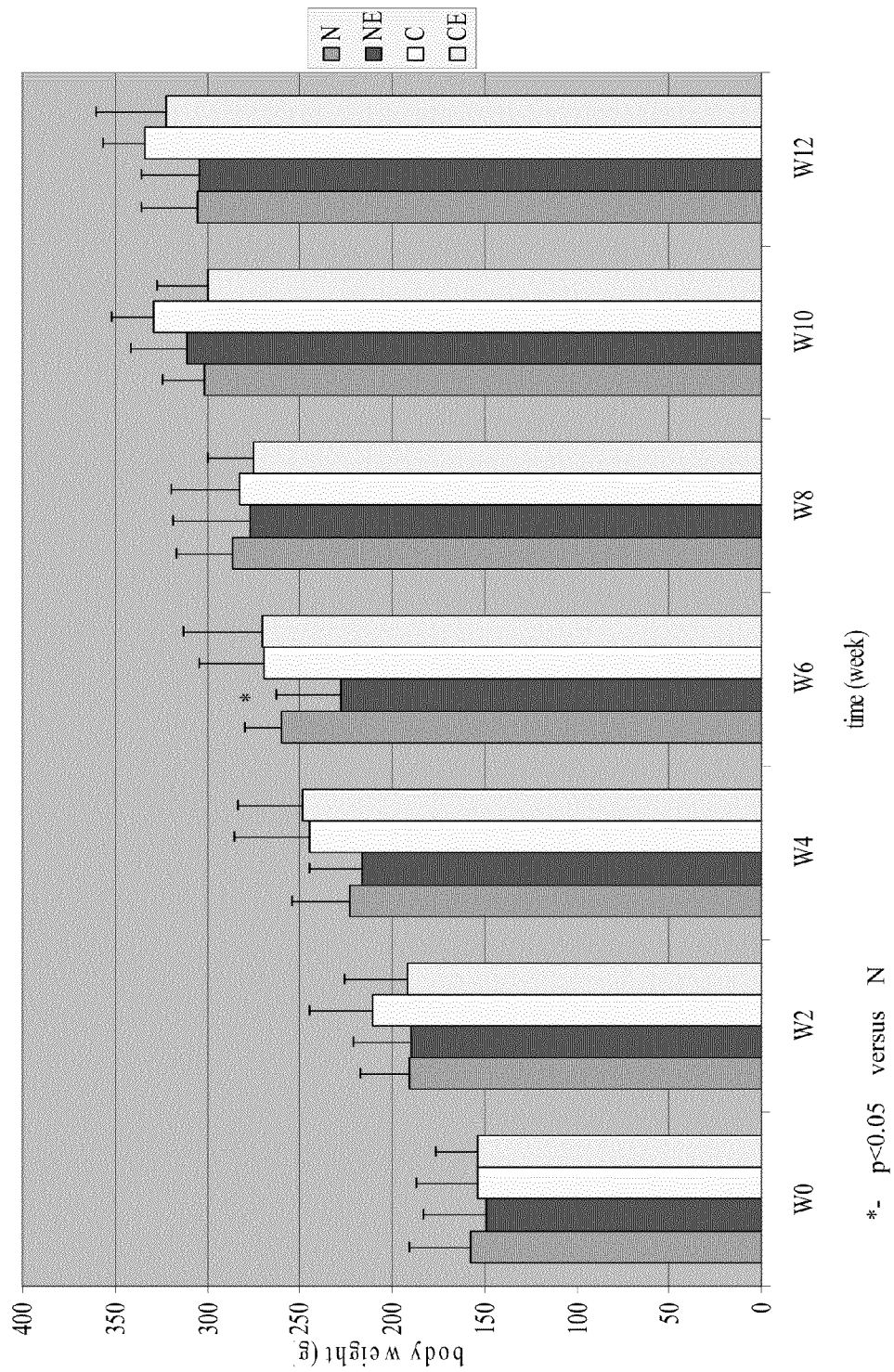

EXTRACT FROM PALM LEAVES AND A METHOD FOR PRODUCING THE SAME

FIELD OF THE INVENTION

The present invention relates to an extract from palm leaves which is capable of preventing or assisting in the management of hypercholesterol, hypertension, hyperlipidemia, atherosclerosis, obesity, oxidative stress, organ damage and other ailments related to or caused by such conditions of an individual upon use of the extracts or pertaining products.

BACKGROUND OF THE INVENTION

Cardiovascular related diseases are becoming an increasing health concern in modern population. One of the main causes of cardiovascular disease is bad dietary habit and sedentary lifestyle, especially over consumption of food with high cholesterol, fat or excessive calories. Lack of daily physical activities and exercises have further advanced the diseased state. Nevertheless, genetic disorder such as familial hypercholesterolemia, hypertension, obesity and diabetes also predisposes the inherited individuals to cardiovascular problems prior to the intervention of the external environmental factors. Though there are numeral pharmaceutical products available commercially for treatment and alleviation of the related cardiovascular problems, it is ideal to have daily dietary product which are capable of either preventing the advancement of the cardiovascular diseases or improving the cardiovascular system of an individual upon regular use of such comestible products.

Researches have shown that metabolites from different plant species contain proven properties in preventing against cardiovascular diseases. Subsequently, different health-promoting products containing the plants metabolites as the active ingredients have been developed. For example, Villoo et al. have filed a patent application WO2006090198 which parts of the claims are directed to a comestible product incorporated with an extract from the plant of *Terminalia arjuna*. This application has claimed that the extract of the *Terminalia arjuna* is capable of treating cardiovascular disease upon consumption of the extract.

Another Japanese patent no. 9206043 filed another application regarding the preparation and method to produce hemp palm tea which employs simple processes for the preparation of leaves derive from the plants of hemp palm family for use as tea.

United State patent no. 2007036821 is another application related to an extract from the seaweed to be consumed for its anti-thrombotic properties. This application has claimed the utilization of the extract from the seaweed in preparing foodstuff such as cereals, bread, drinks, health bars, juices, concentrates, canned food, ice cream and the like.

Bulgaria patent no. 100600 claims a dietetic food to be consumed as the prophylaxis of degenerative and ischemic diseases related to cardiovascular which constituted of hawthorn extract and natural bee honey as the major components to carry out the claimed effects.

SUMMARY OF THE INVENTION

The present invention aims to provide a plant or herbal extract which is suitable to be incorporated into daily diet for improving cardiovascular system upon use of the products.

Further object of the present invention is to disclose a method to improve cardiovascular system or prevent cardiovascular related diseases (one or more effects such as anti-hypertensive, anti-atherogenic, anti-hypercholesterol, anti-obesity, anti-hyperlipidemic, anti-oxidative, vasorelaxant and the like) by administrating the aforesaid herbal extract or its derivatives products orally to a subject.

Still another object of the present invention is to disclose an extraction method specifically useful in isolating the desired phenolic compounds/flavonoids from the foliages of the plants of Arecaceae family. The disclosed method is able to isolate the active plant metabolites and provide efficient yield without degrading its therapeutic effect for cardiovascular disease protection.

At least one of the preceding objects is met, in whole or in part, by the present invention, in which one of the embodiment of the present invention is a comestible composition for promoting healthcare of cardiovascular system of an individual comprises an extract derives from foliages of a plant of Arecaceae family using a polar extraction solvent.

Further embodiment of comestible composition is preferably having the extract prepared in a concentrated form thus can be conveniently incorporated to the products.

In order to effectively isolate out the desired metabolites from the plants of the Arecaceae family, the preferred polar extraction solvent is selected from the group consisting of water, alcohol, acetone, chloroform and any combination thereof.

Further embodiment of the present invention is regarding a method for promoting healthcare of cardiovascular system in a subject comprising the step of administrating orally the subject an effective amount of an extract of foliages derived from a plant of Arecaceae family using an organic extraction solvent.

The present invention also discloses a method for preparing an herbal extract comprising the steps of soaking dried foliages derive from a plant of Arecaceae family into a polar solvent; removing the soaked dried foliages from the polar solvent; and concentrating the polar solvent to acquire the herbal extract.

Similarly, the polar solvent found to be efficient in the extraction is any one or combination of water, alcohol, acetone and chloroform.

Further embodiment to improve the extraction efficiency involve a pre-treatment step of fragmentizing the dried foliages into small fragment or pulverizing to paste or powdery form before soaking into the polar extraction solvent.

Still another embodiment of the present invention, the foliages of the plant of Arecaceae family is preferably derived from any one or combination of the species, but not limited to, *Elaeis guineensis*, *Elaeis oleifera*, *Phoenix dactylifera* and *Cocos nucifera*.

BRIEF DESCRIPTION OF THE DRAWINGS

FIG. 1 is a graph showing the body weight of the tested Sprague Drawley rats at different interval of the experiments; FIG. 2($b$) is a graph showing absence of hypotensive effect or toxicity of the comestible product given to the normal tested rat groups which had not been induced hypertension.

DETAILED DESCRIPTION OF THE INVENTION

Figure 2A:
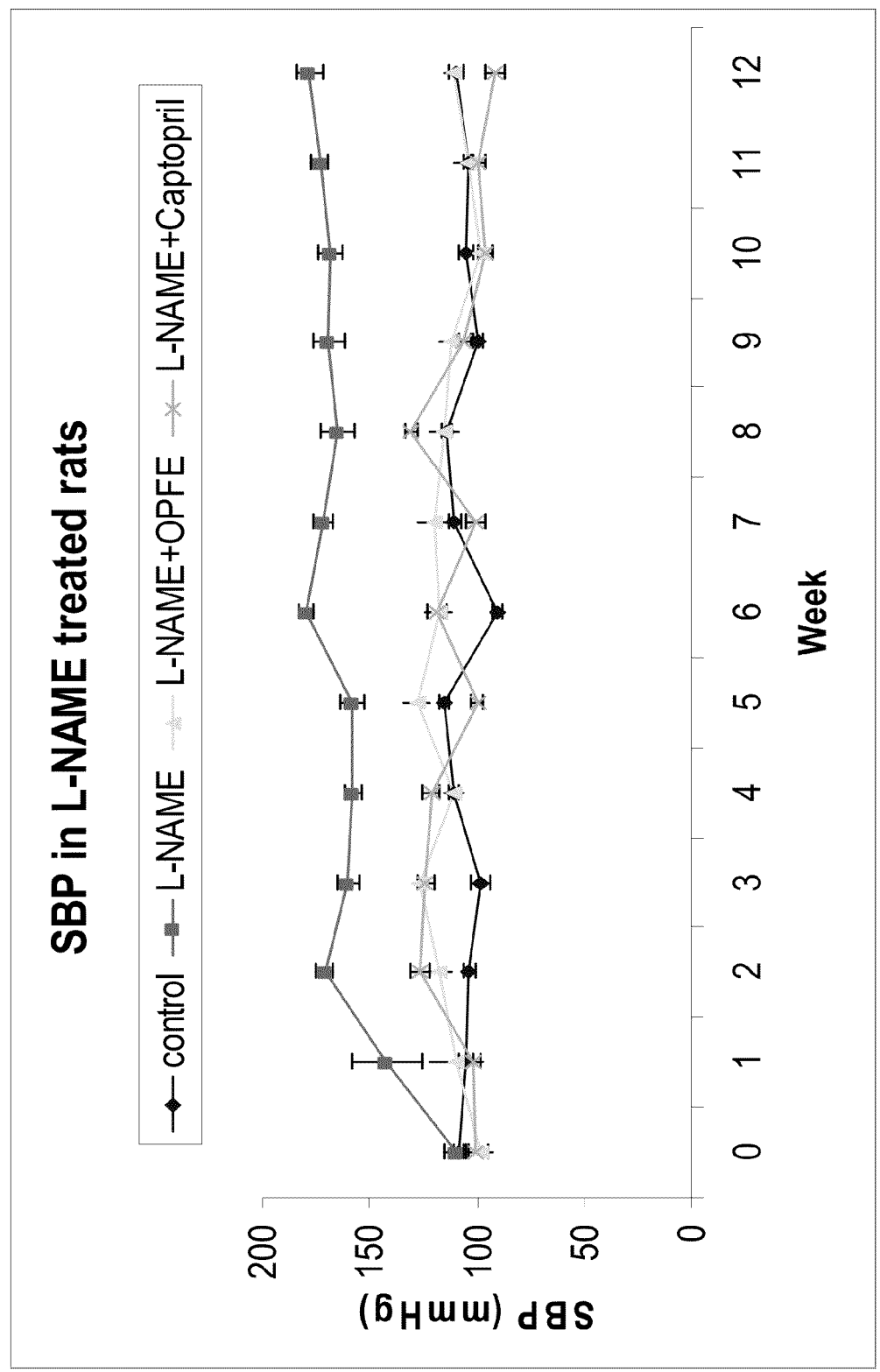
FIG. 2($a$) is a graph showing the antihypertensive effect of the product given to the tested rat groups which is treated with Nω-nitro-L-arginine methyl ester (L-NAME) for inducing hypertension.

One skilled in the art will readily appreciate that the present invention is well adapted to carry out the objects and obtain the ends and advantages mentioned, as well as those inherent therein. The embodiment describes herein is not intended as limitations on the scope of the invention.

The term "promoting healthcare of cardiovascular system" used herein throughout the specification refers to the one or more effects such as anti-hypertensive, anti-atherogenic, anti-hypercholestrol, anti-obesity, anti-hyperlipidemic, anti-oxidative, vasorelaxant and the like. The aforementioned effects can be initiated variedly upon different ingested amount or dose, form of supply of the extract, coupled with other components, age and sex of the administrated subject and so on.

The term "pharmaceutically effective amount" used herein through out the specification refers to the amount of the active ingredient, the extract, to be administered orally to the subject to trigger the desired effect without or causing minimal toxic adverse effect against the subject. One skilled in the art should know that the effective amount can vary from one individual to another due to the external factors such as age, sex, diseased state, races, body weight, formulation of the extract, availability of other active ingredients in the formulation and so on.

In respect to the preferred embodiment of the present invention, a method for preparing an herbal extract from a plant of Arecaceae family is disclosed. The method basically comprises the steps of pre-treating foliages from a plant of Arecaceae family; extracting the pre-treated foliages using a polar solvent; removing the pre-treated foliages from the used polar solvent; and concentrating the used polar solvent to acquire the herbal extract. The disclosed method is found to be effective in isolating the favored phenolic compounds/flavonoids, peptides or active metabolites which provides a therapeutic effect or health promoting effect towards the cardiovascular system upon ingestion orally of a subject.

According to another preferred embodiment of the disclosed method, the foliages are pre-treated before subjecting to extraction. The pre-treatment process may involve a washing step to clean any dirt or physical pollutants captured at the surface of the foliages. Other pretreatment step is preferably reducing the moisture content of the foliages by any known means or approaches in the art to improve the extraction rate and yield. In the preferred embodiment, the foliages are subjected to drying in an oven at 40-120° C. The drying temperature shall not be set too high as such practice may degrade the active metabolites and phenolic compounds/flavonoids contained within the foliages. The preferred temperature shall range from 40° C. to 60° C. Other pretreatment steps that can be employed are preparing the dried foliages into small fragments, or pulverization to paste or powdery form prior to the soaking step. The fragmentized portion or pulverized leaves can greatly increase the available contact surface of the dried foliages that are exposed to polar extraction solvent thus enhance the rate as well as the yield of the extraction method. Possibly, the pre-treated foliages may be subjected to a plurality occasion of extraction using different types of polar extraction solvent to obtain the optimal yield.

Though mere soaking the pre-treated foliages into the polar extraction solvent shall enable the extraction of the preferred phenolic compounds/flavonoids due to the polarity attraction of the extraction solvent, the process may be accelerated by stirring the extraction mixture, or the use of heat and pressure, both of the extraction solvent and the pre-treated foliages, during the time the extraction is conducted. It is important to note that the extracted phenolic compounds/flavonoids from the foliages are mainly constituted of polyphenols, small peptides and other bioactive compounds. Therefore, the efficiency rate of the extraction is sensitive towards pH changes in the extraction solvent. In the most preferred embodiment of the disclosed method, the pH of the extraction content shall fall within the interval of pH 1 to 10, most preferred pH 3 to 8, for achieving optimal yield and extraction rate. Preferably, the pH of the extraction solvent is monitored closely during the extraction to ensure that the pH of the extraction solvent favors the reaction. Any shift of the pH can be adjusted back to the preferred range by using pH adjusters such as hydrochloric acid, sodium hydroxide, and the like. Moreover, applying appropriate amount of heat energy to the extraction system is another feasible approach to enhance the extraction rate and yield. Relying upon the polar solvent utilized, the heating is most preferred within the range of 40° C. to 120° C. Precaution should be taken into consideration that denaturalization possibly occurs at high temperature of heating.

It is important to be noted that the foliages used in the disclosed method in the preferred embodiment derives from the plant species of, but not limited to, *Elaeis guineensis, Elaeis oleifera, Phoenix dactylifera* and *Cocos nucifera*. The extracts obtained from the abovementioned plant species are found pleasant in both taste and fragrance thus render them suitable to be incorporated into edible products especially comestibles.

Pursuant to further embodiment of the disclosed method, the polar extraction solvent preferably employed is, but not limited to, any one or combination of water, alcohol, acetone and chloroform. The desired phenolic compounds/flavonoids to be extracted from the foliages are mainly constituted of, but not limited to, polyphenols and small peptides. Due to high polarity of these phenolic compounds/flavonoids, the polar solvent is found to be the effective in extracting these desired compounds from the plant matrix. To acquire optimal yield by using effective amount of polar extraction solvent, the ratio the pre-treated foliages to the polar extraction solvent is preferably 1-3:6-10 (w/v).

Preferably, the pre-treated foliages after subjecting to extraction can be separated by any known means and approaches in the art for disposal. Vacuum filtration is most preferred as such approach is commonly available. Similarly, vaporization of the used polar extraction solvent to concentrate phenolic compounds/flavonoids can be performed by different approaches. For, example drying the used extraction solvent using heat energy or vacuum drying. Concentrating the phenolic compounds/flavonoids by dissipating the used extraction polar solvent shall finally reach to the stage where the phenolic compounds/flavonoids is concentrated to a paste or powdery form. This paste or powdery form of phenolic compounds/flavonoids extract can then be utilized for various applications.

Attention is now drawn to another embodiment of the present invention which involves a comestible composition for promoting healthcare of cardiovascular system of an individual comprises extracts derive from foliages of a plant of Arecaceae family using a polar extraction solvent. The comestibles mentioned herein can be any common daily consumed processed food such as bread, noodles, confections, chocolates, beverages, and the like. One skilled in the art shall appreciate the fact that the aforesaid extract can be incorporated into the processed comestibles during the course of food processing. Therefore, any modification thereon shall not depart from the scope of the present invention.

As setting forth in the above description, the foliages used for preparing the extract are derived from the plants of Arecaceae family. More preferably, the plant is any one or combination of the plant species of, but not limited to, *Elaeis guineensis, Elaeis oleifera, Phoenix daciylifera* and *Cocos nucifera*. The inventors of the present invention discovered that the extract derives from the aforementioned species possesses both pleasant taste and fragrance that confers the derived extract to be comfortably incorporated with the comestibles product with minimal additional refining process.

According to the preferred embodiment, the extract to be incorporated into the comestibles can be acquired from any known method not limited only to the foregoing disclosed method. Following to another embodiment, the extract is prepared in a concentrated form, preferably paste or powdery form which enables the extract to be prepared in various formulations of the comestibles.

In line with the preferred embodiment, the extract shall be the plant metabolites which are susceptible to a polar extraction solvent. The phenolic compounds/flavonoids and small peptides with the cardiovascular system health-promoting properties are those metabolites with high polarity in the foliages. Therefore, the extract from the foliages of plants of Arecaceae family is preferably derives from the polar extraction solvent of water, alcohol, acetone, chloroform and any combination thereof.

In view of the prominent property of promoting healthcare of cardiovascular system of the extract, further embodiment of the present invention includes a method for promoting healthcare of cardiovascular system in a subject comprising the step of administrating orally the subject an effective amount of an extract of foliages derive from a plant of Arecaceae family using a polar extraction solvent. From the experiments conducted, it is clear that the extract employed in this embodiment shows antihypertensive, anti-oxidative, anti-atherogenic, anti-hypercholestrol, anti-hyperlipidemic, anti-obesity, vasorelaxant and similar effects. Moreover, the plant of Arecaceae family is any one or combination of, but not limited to, *Elaeis guineensis, Elaeis oleifera, Phoenix dactylifera* and *Cocos nucifera*.

Upon intake of the extract, the ingested composition not only acts like prophylaxis to prevent development or advancement of the cardiovascular diseases, but also function as therapeutic composition to relieve or even heal the diseased state.

The following example is intended to further illustrate the invention, without any intent for the invention to be limited to the specific embodiments described therein.

EXAMPLE 1

The extraction conditions were conducted as follows:
Oil palm leaves were collected, cleaned, washed and cut into small pieces and oven dried at 40° C. overnight. The dried material was ground using a blender and extracted three times with alcohol (1:10 v/v) and three times with acetone or with mixtures of chloroform and alcohol. Other solvent may be used as a medium for the polyphenols extraction. This is a process designed to separate soluble phenolic compound by diffusion from a solid matrix (plant tissue) using a liquid matrix (solvent). Alcohol, chloroform and acetone has produced good yield in extracting flavones, flavonols, and catechin. The extraction was done a few times. The pooled extracts were vacuum-dried at 40° C. and stored until used.

EXAMPLE 2

Anti-hypertensive, anti-atherogenic, anti-hypercholesterol, anti-obesity, anti-hyperlipidemic, antioxidative and organ protective properties evaluation had been conducted on the different products from the different source of palm leaves.

The anti-obesity, anti-hyperlipidemic, anti-hypercholesterol, and anti-atherogenic properties of palm leaves extract and palm leaves functional ingredients are described. Animals on high-cholesterol diet supplemented with palm leaves extract and palm leaves functional ingredients for 12 weeks, showed lower body weight gain, lower total plasma cholesterol (TC), lower plasma triglycerides (TG) and lower bad Low Density lipoprotein Cholesterol and lower plasma malondialdehyde (MDA) which are the products of lipid oxidation that can react with protein, DNA and cell membranes, causing further organ and tissue damage (FIG. 1 and Table 1). High cholesterol diet animals supplemented with palm leaves extract and palm leaves functional ingredients particularly oil palm leaves showed a trend of increased plasma good high density lipoprotein cholesterol (HDL-C), and lower AI (atherogenic index) compared to animals on high cholesterol diet alone. These palm leaves extract (both instant and herbal tea) and palm leaves functional ingredients showed significant anti-obesity, anti-hyperlipidemic, antioxidative, lower Atherogenic index, anti-hypercholesterol effect, anti-hypertension and organ protective effects for use as functional beverage palm extract and palm leaves functional ingredients for reducing degenerative diseases risks.

The palm leaves extract and palm leaves functional ingredients supplemented animals on high-cholesterol diet showed significant lower body weight gain as compared to animals fed on high-cholesterol diet (C) alone (Table 1). The palm leaves extract and palm leaves functional ingredients supplemented animals on normal diet showed no significant differences in body weight gain as compared to the normal diet animals suggesting that these palm leaves extract and palm leaves functional ingredients do not significantly increase or decrease body weight of normal healthy animals.

The animals fed on high-cholesterol diet (C), had their plasma TC increased by 67% in 6 weeks and 83% in 12 weeks which were significantly higher than normal control animals (N). The animals fed on high-cholesterol diet supplemented with palm leaves extract and palm leaves functional ingredients showed lower plasma TC value (lower by −61%) as compared to animals fed on high-cholesterol diet alone (C). The plasma TC value in normal animals supplemented with palm leaves extract and palm leaves functional ingredients (NE, NC and NS) showed no significant difference with animals fed on control diet (N). There was an increase of plasma TG level of animals fed with high-cholesterol diet alone (C) from the beginning till the end of the experiment (12 weeks). After 12 weeks, animals on high cholesterol diet supplemented with palm leaves extract and palm leaves functional ingredients showed a significant lower plasma TG level of −66% as compared to animals without supplementation (C).

Table 1 shows, plasma HDL-C of high-cholesterol fed animals supplemented with palm leaves extract and palm leaves functional ingredients (CE) were significantly higher than high-cholesterol diet alone (C). The plasma HDL-C in high-cholesterol fed animals supplemented with palm leaves extract and palm leaves functional ingredients showed a significant increase of 60% compared to high-cholesterol diet (C) alone. The high-cholesterol group (C) showed significantly higher LDL-C level as compared to the control group (N). The plasma LDL-C in high-cholesterol fed animals supplemented with palm leaves extract and palm leaves functional ingredients showed a significant decrease of −61% relative to animals fed on high-cholesterol diet (C) alone.

The data demonstrated that animals fed on high cholesterol diet supplemented with palm leaves extract and palm leaves functional ingredients reduced the levels of plasma TC and LDL-C. In addition the results showed that animals fed on high cholesterol diet supplemented with palm leaves extract and palm leaves functional ingredients (particularly oil palm leaves) increased the concentration of HDL-C when compared with high cholesterol diet (C) alone. High-cholesterol diet supplemented with palm leaves herbal tea showed a trend of increased plasma HDL-C, reduced TG, reduced LDL-C lipid peroxidation. High lipid peroxidation as indicated by the terminal product MDA, is associated with high oxidative injury by free radicals and oxidative status.

TABLE 1

|  | N | NE | C | CE |
|---|---|---|---|---|
| Total cholesterol(mmol/L) | | | | |
| Week 0 | 1.38 ± 0.15 | 1.38 ± 0.29 | 1.38 ± 0.11 | 1.35 ± 0.27 |
| 2 | 1.37 ± 0.28 | 1.28 ± 0.18 | 1.67 ± 0.26* | 1.41 ± 0.22 |
| 4 | 1.18 ± 0.09 | 1.13 ± 0.12 | 1.77 ± 0.43* | 1.65 ± 0.39* |
| 6 | 1.37 ± 0.11 | 1.22 ± 0.12 | 2.25 ± 0.48* | 1.89 ± 0.28* |
| 8 | 1.38 ± 0.33 | 1.15 ± 0.11* | 2.55 ± 0.37* | 1.49 ± 0.26# |
| 10 | 1.39 ± 0.18 | 0.87 ± 0.11* | 2.52 ± 0.33* | 1.47 ± 0.39# |
| 12 | 1.45 ± 0.2 | 1.12 ± 0.17 | 2.88 ± 0.53* | 1.12 ± 0.36# |
| HDL-Cholesterol(mmol/L) | | | | |
| Week 0 | 0.57 ± 0.09 | 0.57 ± 0.17 | 0.58 ± 0.07 | 0.55 ± 0.08 |
| 2 | 0.54 ± 0.09 | 0.62 ± 0.09* | 0.70 ± 0.10 | 0.69 ± 0.07 |
| 4 | 0.72 ± 0.20 | 0.75 ± 0.06 | 0.83 ± 0.07 | 0.85 ± 0.05 |
| 6 | 0.53 ± 0.04 | 0.77 ± 0.06* | 0.56 ± 0.10 | 0.96 ± 0.08*# |
| 8 | 0.64 ± 0.1 | 0.77 ± 0.03* | 0.60 ± 0.09 | 0.79 ± 0.14*# |
| 10 | 0.64 ± 0.11 | 0.68 ± 0.02 | 0.65 ± 0.12 | 0.76 ± 0.21# |
| 12 | 0.64 ± 0.19 | 0.70 ± 0.12* | 0.55 ± 0.04* | 0.88 ± 0.19*# |
| TC/HDL-Cholesterol ratio | | | | |
| Week 0 | 2.47 ± 0.51 | 2.53 ± 0.92 | 2.42 ± 0.36 | 2.57 ± 0.82 |
| 2 | 2.46 ± 0.36 | 2.07 ± 0.46* | 2.38 ± 0.75 | 2.04 ± 0.34* |
| 4 | 1.93 ± 0.43 | 1.48 ± 0.22* | 2.15 ± 0.52 | 1.73 ± 0.30*# |
| 6 | 1.95 ± 0.16 | 1.57 ± 0.16* | 2.29 ± 0.81 | 1.96 ± 0.46 |
| 8 | 1.86 ± 0.19 | 1.43 ± 0.09* | 1.61 ± 0.52 | 1.43 ± 0.21* |
| 10 | 1.77 ± 0.35 | 1.32 ± 0.19* | 1.62 ± 0.42 | 1.40 ± 0.24* |
| 12 | 1.71 ± 0.29 | 1.39 ± 0.37* | 1.66 ± 0.77 | 1.49 ± 0.27* |
| LDL-Cholesterol(mmol/L) | | | | |
| Week 0 | 0.31 ± 0.09 | 0.36 ± 0.17 | 0.27 ± 0.03 | 0.26 ± 0.06 |
| 2 | 0.25 ± 0.09 | 0.27 ± 0.04 | 0.32 ± 0.09 | 0.29 ± 0.08 |
| 4 | 0.24 ± 0.04 | 0.26 ± 0.06 | 0.41 ± 0.06* | 0.41 ± 0.10* |
| 6 | 0.29 ± 0.03 | 0.26 ± 0.02 | 0.52 ± 0.08* | 0.42 ± 0.14 |
| 8 | 0.26 ± 0.006 | 0.26 ± 0.03 | 0.56 ± 0.006* | 0.35 ± 0.08# |
| 10 | 0.25 ± 0.02 | 0.23 ± 0.05 | 0.55 ± 0.02* | 0.29 ± 0.04# |
| 12 | 0.27 ± 0.06 | 0.23 ± 0.03 | 0.57 ± 0.06* | 0.22 ± 0.06# |
| Triglycerides(mmol/L) | | | | |
| Week 0 | 0.9 ± 0.09 | 0.86 ± 0.08 | 0.90 ± 0.10 | 0.91 ± 0.14 |
| 2 | 0.87 ± 0.11 | 0.81 ± 0.22 | 0.79 ± 0.08 | 0.64 ± 0.10 |
| 4 | 0.75 ± 0.19 | 0.63 ± 0.07 | 0.71 ± 0.18 | 0.60 ± 0.13 |
| 6 | 0.58 ± 0.09 | 0.58 ± 0.10 | 0.71 ± 0.10 | 0.64 ± 0.14 |
| 8 | 0.55 ± 0.08 | 0.55 ± 0.05 | 0.81 ± 0.10* | 0.62 ± 0.03 |
| 10 | 0.43 ± 0.16 | 0.45 ± 0.06 | 0.85 ± 0.09* | 0.47 ± 0.09# |
| 12 | 0.49 ± 0.05 | 0.42 ± 0.05* | 0.86 ± 0.07* | 0.39 ± 0.06*# |

*$p < 0.05$ versus N control,
$p < 0.05$ versus C control levels and lower atherogenic index (AI) as compared to high-cholesterol group without palm leaves extract and palm leaves functional ingredients supplementation.

Atherogenic index (Table 1) expressed by the ratio of LDL-C/HDL-C, significantly decreased in high-cholesterol diet supplemented with palm leaves extract and palm leaves functional ingredients as compared to high-cholesterol diet alone. These effects is beneficial as the observed decreased in these indices indicate that palm leaves extract and palm leaves functional ingredients play an important protective role in reducing risk against atherosclerosis and CVD.

The animals fed on high-cholesterol diet (C) showed higher MDA levels compared to control animals (N), especially the MDA elevation at week 12. Animals fed on high-cholesterol diet supplemented with Palm leaves extract and palm leaves functional ingredients showed significantly lower MDA level as compared to animals without supplementation (C) after 12 weeks, indicating that these palm leaves extract and palm leaves functional ingredients retarded

EXAMPLE 3

The anti-oxidative properties of palm leaves extract and palm leaves functional ingredients are described in Table 2, 3 an 4.

Table 2 shows that the erythrocytes SOD, GSH-Px, and CAT activities of hypertensive animals (SHR) were significantly increased compared to control normotensive animals (N) indicating increased oxidative states of the animals. The hypertensive animals (SHR) supplemented with palm leaves extract and palm leaves functional ingredients, (SHR+OPLE) showed significant reduced erythrocytes SOD, GSH-Px, and CAT activities, bringing it back to near normal levels of normotensive animals. SOD, GSH-Px, and CAT is the first line of antioxidative enzyme defense against oxidative stress, converting reactive oxygen to hydrogen peroxide and water. SOD, GSH-Px, and CAT reduced activity indicate reduced oxidative stress in hypertensive animals supplemented with oil palm leaves extract. Similar results were observed in the organs most commonly affected by hypertension namely kidneys, hearts and brain.

TABLE 2

| Group | Week 0 | Week 6 | Week 8 | Week 12 |
|---|---|---|---|---|
| Erythrocyte CuZn-SOD (U/ml) | | | | |
| Control normotensive | 0.013 ± 0.0008 | 0.023 ± 0.0011 | 0.016 ± 0.0014 | 0.020 ± 0.0007 |
| OPLE | 0.015 ± 0.0012 | 0.023 ± 0.0010 | 0.018 ± 0.0007 | 0.020 ± 0.0010 |
| Captopril | 0.014 ± 0.0010 | 0.022 ± 0.0006 | 0.015 ± 0.0019 | 0.018 ± 0.0006 |
| SHR (hypertensive) | 0.020 ± 0.0006* | 0.010 ± 0.0010* | 0.013 ± 0.0015* | 0.007 ± 0.0012* |
| SHR + OPLE | 0.022 ± 0.0008* | 0.009 ± 0.0007* | 0.011 ± 0.0006* | 0.011 ± 0.0013* |
| SHR + captopril | 0.019 ± 0.0012* | 0.009 ± 0.0012* | 0.011 ± 0.0004* | 0.012 ± 0.0007*# |
| Erythrocyte Glutathione Peroxidase | | | | |
| Control normotensive | 19.8 ± 3.81 | 18.8 ± 3.26 | 20.0 ± 5.78 | 24.2 ± 4.17 |
| OPLE | 20.7 ± 3.16 | 25.2 ± 3.77 | 22.6 ± 4.91 | 27.0 ± 7.93 |
| Captopril | 16.5 ± 0.76 | 21.1 ± 5.05 | 9.3 ± 1.24 | 26.2 ± 6.90 |
| SHR (hypertensive) | 32.46 ± 3.72 | 19.95 ± 1.36 | 40.05 ± 2.39* | 43.26 ± 0.81* |
| SHR + OPLE | 29.13 ± 2.25 | 18.1 ± 1.64 | 34.9 ± 3.9# | 31.41 ± 3.36# |
| SHR + captopril | 31.47 ± 0.94 | 12.69 ± 2.47 | 28.77 ± 2.05# | 34.63 ± 2.2# |
| Erythrocyte Catalase (k/ml) | | | | |
| Control normotensive | 0.013 ± 0.0007 | 0.014 ± 0.0011 | 0.013 ± 0.0004 | 0.014 ± 0.0005 |
| OPLE | 0.013 ± 0.0007 | 0.014 ± 0.0013 | 0.016 ± 0.0007* | 0.018 ± 0.0008* |
| Captopril | 0.014 ± 0.0006 | 0.013 ± 0.0003 | 0.014 ± 0.0005 | 0.013 ± 0.0008 |
| SHR (hypertensive) | 0.017 ± 0.0006* | 0.015 ± 0.001 | 0.019 ± 0.0006* | 0.015 ± 0.0006 |
| SHR + OPLE | 0.017 ± 0.0006* | 0.016 ± 0.0003* | 0.017 ± 0.0002*# | 0.017 ± 0.0008* |
| SHR + captopril | 0.019 ± 0.0007* | 0.017 ± 0.0003* | 0.017 ± 0.0004* | 0.016 ± 0.0003* |

Control = normotensive animals;
OPLE = normotensive animals treated with oil palm leaves extract;
captopril = normotensive animals treated with captopril;
SHR = spontaneous/genetically hypertensive animals;
SHR + OPLE = SHR treated with OPLE;
SHR + captopril = SHR treated with captopril.
*p < 0.05 versus normotensive control,
p < 0.05 versus hypertensive SHR.

TABLE 3

| Group | Kidney | Heart | brain |
|---|---|---|---|
| Organ CuZn-SOD (U/mg protein) | | | |
| Control normotensive | 2.37 ± 0.113 | 3.91 ± 0.071 | 6.41 ± 0.342 |
| SHR (hypertensive) | 2.34 ± 0.087 | 3.50 ± 0.110 | 6.40 ± 0.823 |
| SHR + OPLE | 0.67 ± 0.053*# | 0.70 ± 0.278*# | 0.42 ± 0.214*# |
| SHR + captopril | 0.80 ± 0.199*# | 0.78 ± 0.301*# | 1.26 ± 0.097*# |
| Organ GPx (U/mg protein) | | | |
| Control normotensive | 2.42 ± 0.125 | 3.35 ± 0.712 | 7.30 ± 0.640 |
| SHR (hypertensive) | 2.88 ± 0.398 | 4.56 ± 0.451 | 6.53 ± 1.457 |
| SHR + OPLE | 1.72 ± 0.16*# | 3.00 ± 0.282# | 3.25 ± 0.503* |
| SHR + captopril | 2.02 ± 0.184# | 3.20 ± 0.23 | 2.87 ± 0.360*# |
| Organ Catalase (k/mg protein) | | | |
| Control normotensive | 26.87 ± 2.83 | 4.39 ± 0.555 | 2.47 ± 0.305 |
| SHR (hypertensive) | 29.4 ± 3.42 | 4.297 ± 0.262 | 1.79 ± 0.833 |
| SHR + OPLE | 25.75 ± 1.00 | 3.20 ± 0.198 | 1.90 ± 0.172 |
| SHR + captopril | 25.96 ± 2.04 | 4.08 ± 0.458 | 1.96 ± 0.27 |

Control = normotensive animals;
OPLE = normotensive animals treated with oil palm leaves extract;
captopril = normotensive animals treated with captopril;
SHR = spontaneous/genetically hypertensive animals;
SHR + OPLE = SHR treated with OPLE;
SHR + captopril = SHR treated with captopril.
*P < 0.05 versus normotensive control;
P < 0.05 versus hypertensive SHR.

EXAMPLE 4

The anti-hypertensive and protective properties of the palm leaves herbal tea (both instant and leaves) extract and palm leaves functional ingredients on L-NAME induced hypertensive animals are shown in the FIG. 2 below.

Blood Pressure

Figure 2B:
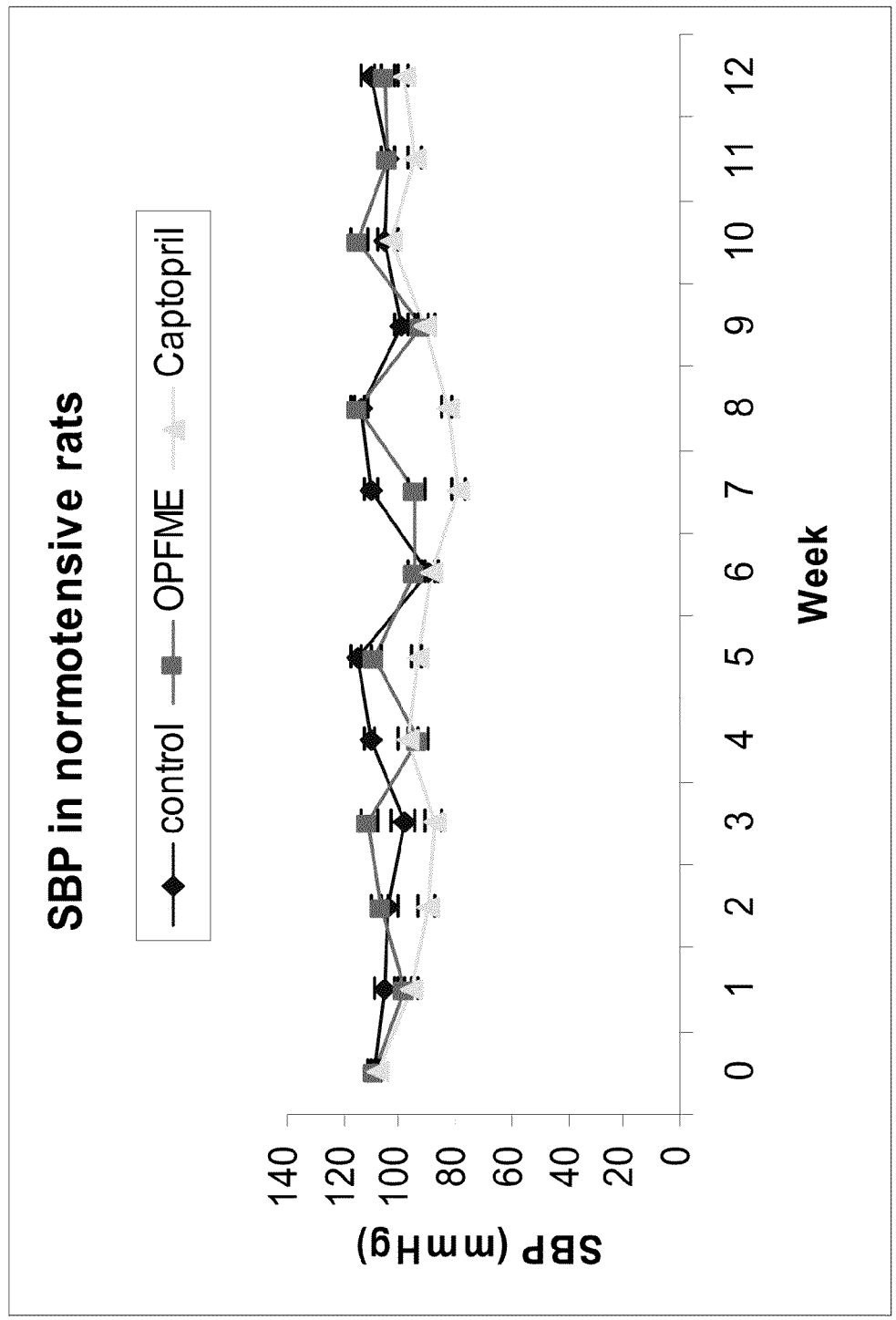

FIG. 2 summarizes BLOOD PRESSURE data in L-NAME induced hypertensive groups. Treatment with L-NAME induced a time-dependent rise in blood pressure, which was significantly attenuated by co administration of original palm leaves extract (OPLE). SYSTOLIC BLOOD PRESSURE (SBP) was lower in L-NAME+OPLE animals right from week 1 throughout the study and remained in the normal range (<140 mmHg), versus values in animals not treated with OPLE. The attenuation was similar to those of L-NAME+the anti-hypertensive drug captopril and control normotensive animals. SYSTOLIC BLOOD PRESSURE, however, was not lowered in normotensive animals supplemented with OPLE (FIG. 2).

EXAMPLE 5

The organ protective properties of the palm leaves extract and palm leaves functional ingredients on heart, and kidneys are shown in the morphology Table 4 below.

All SHR groups had significantly lower body weight versus control. Kidney/BW were similar in all groups. Heart/BW values in L-NAME+OPLE rats did not significantly differ from those of L-NAME rats. However, in L-NAME+captopril rats had lower Heart/BW ratio versus L-NAME. Heart/BW ratios of SHR and SHR+captopril were significantly higher than those of control rats whereas in SHR+OPLE rats the ratio was significantly lower than those of SHR and similar to control rats

TABLE 4

| Group | Final body weight (g) | Kidney (g) | Kidney/Body Weight (mg/g) | Heart (g) | Heart/Body weight (mg/g) |
|---|---|---|---|---|---|
| Control | 333.4 ± 6.65 | 2.387 ± 0.13 | 7.169 ± 0.0004 | 1.22 ± 0.06 | 3.663 ± 0.0002 |
| OPLE | 325.0 ± 11.1 | 2.150 ± 0.07 | 6.655 ± 0.0003 | 1.26 ± 0.10 | 3.875 ± 0.0003 |
| Captopril | 291.4 ± 8.56 | 2.140 ± 0.07 | 7.370 ± 0.0003 | 1.02 ± 0.04 | 3.558 ± 0.0002 |
| L-NAME | 333.8 ± 13.8 | 2.332 ± 0.11 | 7.321 ± 0.0008 | 1.45 ± 0.19 | 4.544 ± 0.0007 |
| L-NAME + extract | 311.2 ± 23.7 | 1.961 ± 0.15 | 6.366 ± 0.0004 | 1.48 ± 0.11 | 4.796 ± 0.0003 |
| L-NAME + captopril | 296.4 ± 5.97 | 2.017 ± 0.07 | 6.822 ± 0.0002 | 0.91 ± 0.07 | 3.096 ± 0.0003* |
| SHR | 264.9 ± 7.05# | 2.073 ± 0.04 | 7.749 ± 0.0002 | 1.20 ± 0.04 | 4.523 ± 0.0001# |
| SHR + OPLE | 270.33 ± 9.64# | 2.257 ± 0.08 | 8.321 ± 0.0004 | 0.93 ± 0.04+# | 3.453 ± 0.0002+ |
| SHR + captopril | 259.09 ± 5.53# | 2.074 ± 0.09 | 8.139 ± 0.0004 | 1.16 ± 0.07 | 4.533 ± 0.0002# |

L-NAME = Nω-nitro-L-arginine methyl ester;
Data expressed as mean ± SEM
*$P < 0.05$ versus L-NAME induced hypertensive rats
$P < 0.05$ versus normotensive control
+$P < 0.05$ versus SHR (spontaneously/genetically hypertensive rats)

EXAMPLE 6

Beneficial vasorelaxing Nitric Oxide enhancing properties of palm leaves extract and palm leaves functional ingredients.

Table 5 summarizes the nitric oxide values measured in serum of experimental rats. Nitric oxide (NO) levels decreased significantly in L-NAME and L-NAME+OPLE rats versus control rats at week 6. NO were slightly increased in L-NAME+OPLE rats versus values in L-NAME rats. However, by week 8, serum NO in both L-NAME and L-NAME+OPLE rats returned to the level similar to the values in control rats, and maintained until the end of the study. There is a partial increase in NO in L-NAME+OPLE rats compared to L-NAME rats although it was not significant. In SHR+OPLE rats nitric oxide level increased significantly versus both SHR and control rats. By the end of the study only SHR+captopril group had significantly higher nitric oxide level versus control rats

TABLE 5

| Group | Week 0 | Week 6 | Week 8 | Week 12 |
|---|---|---|---|---|
| Control | 0.414 ± 0.024 | 0.548 ± 0.009 | 0.417 ± 0.053 | 0.384 ± 0.038 |
| OPLE | 0.347 ± 0.014 | 0.409 ± 0.109 | 0.468 ± 0.096 | 0.362 ± 0.002 |
| Captopril | 0.381 ± 0.023 | 0.573 ± 0.024 | 0.455 ± 0.060 | 0.525 ± 0.071 |
| L-NAME | 0.339 ± 0.034 | 0.104 ± 0.056 + | 0.276 ± 0.061 | 0.239 ± 0.074 |
| L-NAME + OPLE | 0.319 ± 0.044 | 0.197 ± 0.053 + | 0.283 ± 0.084 | 0.511 ± 0.086 |
| L-NAME + captopril | 0.402 ± 0.008 | 0.585 ± 0.082 * | 0.742 ± 0.123 * | 0.44 ± 0.072 |
| SHR | 0.484 ± 0.01 | 0.516 ± 0.02 | 0.355 ± 0.07 | 0.406 ± 0.13 |
| SHR + OPLE | 0.668 ± 0.14 | 0.349 ± 0.02 | 0.669 ± 0.11 + # | 0.532 ± 0.09 |
| SHR + captopril | 0.230 ± 0.02 | 0.425 ± 0.05 | 0.438 ± 0.08 | 0.572 ± 0.02 + |

SHR = spontaneously hypertensive rats;
+ $P < 0.05$ versus control;
* $P < 0.05$ versus L-NAME;
$P < 0.05$ versus SHR It is to be understood that the present invention may be embodied in other specific forms and is not limited to the sole embodiment described above. However modification and equivalents of the disclosed concepts such as those which readily occur to one skilled in the art are intended to be included within the scope of the claims which are appended thereto.

The invention claimed is:

1. A comestible composition for reducing risk of hypercholesterolemia of an individual comprising an extract derived from foliages of a plant of Arecaceae family *Elaeis guineensis* using a two-step solvent extraction where alcohol is used in the first extraction step and acetone is used in the second extraction step.

2. The comestible composition according to claim 1, wherein the extract is prepared in a concentrated form.

3. The comestible composition according to claim 1 or 2, wherein the two-step solvent extraction is done at a pH of between about 3 and 8.

4. The comestible composition according to claim 1, wherein the two-step solvent extraction is done at a temperature of between about 40° C. and about 120° C.

5. A method of reducing risk of hypercholesterolemia in an individual comprising:

an extract derived from foliages of a plant of Arecaceae family *Elaeis guineensis* using a two-step solvent extraction where alcohol is used in the first extraction step and acetone is used in the second extraction step; and administrating the extract to the individual.

6. The method of claim 5, and further comprising concentrating the extract.

7. The method of claim 5, wherein the two-step solvent extraction is done at a pH of between about 3 and 8.

* * * * *